United States Patent
Okada et al.

(10) Patent No.: US 9,783,493 B2
(45) Date of Patent: Oct. 10, 2017

(54) QUINONE DERIVATIVE AND ELECTROPHOTOGRAPHIC PHOTOSENSITIVE MEMBER

(71) Applicant: KYOCERA Document Solutions Inc., Osaka (JP)

(72) Inventors: Hideki Okada, Osaka (JP); Fumio Sugai, Osaka (JP); Kensuke Kojima, Osaka (JP)

(73) Assignee: KYOCERA Document Solutions Inc., Osaka (JP)

( * ) Notice: Subject to any disclaimer, the term of this patent is extended or adjusted under 35 U.S.C. 154(b) by 0 days.

(21) Appl. No.: 14/953,112

(22) Filed: Nov. 27, 2015

(65) Prior Publication Data

US 2016/0152557 A1    Jun. 2, 2016

(30) Foreign Application Priority Data

Nov. 28, 2014   (JP) .................................. 2014-241218

(51) Int. Cl.
   *G03G 5/00*     (2006.01)
   *C07C 251/24*   (2006.01)
   (Continued)

(52) U.S. Cl.
   CPC .......... *C07C 251/24* (2013.01); *C07D 213/81* (2013.01); *G03G 5/0612* (2013.01); *C07C 2601/16* (2017.05)

(58) Field of Classification Search
   CPC ............................ G03G 5/0612; C07D 213/81
   (Continued)

(56) References Cited

U.S. PATENT DOCUMENTS

2006/0054882 A1    3/2006   Kawakami et al.

FOREIGN PATENT DOCUMENTS

JP   H11-305457      11/1999
JP   2001-022107 A   1/2001
(Continued)

OTHER PUBLICATIONS

An Office Action; "Notice of Reasons for Rejection," issued by the Japanese Patent Office dated Sep. 27, 2016, which corresponds to Japanese Patent Application No. 2014-241218 and is related to U.S. Appl. No. 14/953,112.

*Primary Examiner* — Mark A Chapman
(74) *Attorney, Agent, or Firm* — Studebaker & Brackett PC

(57) ABSTRACT

A quinone derivative represented by general formula (1),

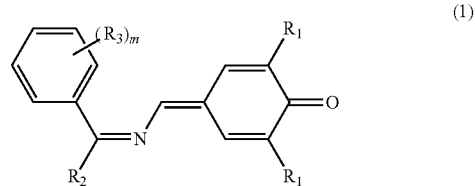

where, in the general formula (1), $R_1$ and $R_2$ each represent, independently of one another, an alkyl group, a cycloalkyl group, an alkoxy group, an aralkyl group, or an aryl group, $R_3$ represents a halogen atom, an alkyl group, an alkoxy group, or an aryl group, m represents an integer of no less than 0 and no greater than 4, and when m represents an integer of no less than 2, chemical groups $R_3$ may be the same as or different from one another.

5 Claims, 3 Drawing Sheets

(51) Int. Cl.
*G03G 5/06* (2006.01)
*C07D 213/81* (2006.01)
(58) Field of Classification Search
USPC .................................... 430/56, 57.1, 58.35
See application file for complete search history.

(56) References Cited

FOREIGN PATENT DOCUMENTS

| | | |
|---|---|---|
| JP | 3576803 B | 7/2004 |
| JP | 2004-341005 A | 12/2004 |
| JP | 2010-175783 A | 8/2010 |
| WO | 2004/006351 A1 | 1/2004 |

QUINONE DERIVATIVE AND ELECTROPHOTOGRAPHIC PHOTOSENSITIVE MEMBER

INCORPORATION BY REFERENCE

The present application claims priority under 35 U.S.C. §119 to Japanese Patent Application No. 2014-241218, filed on Nov. 28, 2014. The contents of this application are incorporated herein by reference in their entirety.

BACKGROUND

The present disclosure relates to a quinone derivative and an electrophotographic photosensitive member.

Electrophotographic photosensitive members are formed from various materials and usable in image forming apparatuses (for example, copiers, facsimile machines, and laser printers) employing the Carlson process. Examples of such electrophotographic photosensitive members include inorganic photosensitive members in which an inorganic material (for example, selenium) is used for a photosensitive layer thereof and organic photosensitive members (organic photoconductors: OPCs) in which an organic material is used for a photosensitive layer thereof. Organic photosensitive members have many advantages such as being inexpensive, highly producible, and environmentally-clean compared to inorganic photosensitive members. Therefore, there has been extensive research on organic photosensitive members.

Examples of organic photosensitive members include a so-called function separation type photosensitive member, that is, a multi-layer photosensitive member in which a charge generating layer and a charge transport layer are stacked on one another, and a so-called single-layer photosensitive member in which a charge generating material and a charge transport material are dispersed in a single photosensitive layer.

Charge transport materials are required to show improved carrier mobility in photosensitive members. Examples of such charge transport materials include hole transport materials. In the meantime, organic photosensitive members are limited to negatively chargeable multi-layer organic photosensitive members having a charge transport layer as an outermost layer for the sake of mechanical strength. However, negatively chargeable organic photosensitive members use negative corona discharge and therefore generate a large amount of ozone, causing a problem such as pollution of the environment and deterioration of the photosensitive members.

In order to overcome such a disadvantage, use of an electron transport material as a charge transport material has been considered. For example, use of a phenylbenzofuranone derivative as an electron transport material for an electrophotographic photosensitive member has been proposed.

SUMMARY

A first embodiment of the present disclosure is a quinone derivative represented by general formula (1) shown below.

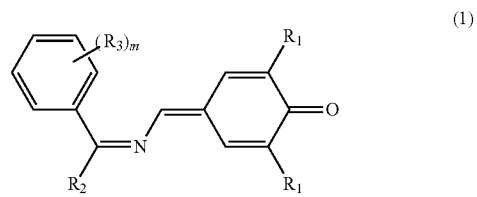

In the general formula (1), $R_1$ and $R_2$ each represent, independently of one another, an alkyl group having a carbon atom number of no less than 1 and no greater than 10, a cycloalkyl group having a carbon atom number of no less than 3 and no greater than 10, an alkoxy group having a carbon atom number of no less than 1 and no greater than 6, an aralkyl group having a carbon atom number of no less than 6 and no greater than 12, or an optionally substituted aryl group having a carbon atom number of no less than 6 and no greater than 14. $R_3$ represents a halogen atom, an optionally substituted alkyl group having a carbon atom number of no less than 1 and no greater than 6, an optionally substituted alkoxy group having a carbon atom number of no less than 1 and no greater than 6, or an optionally substituted aryl group having a carbon atom number of no less than 6 and no greater than 14. m represents an integer of no less than 0 and no greater than 4. When m represents an integer of no less than 2, chemical groups $R_3$ may be the same as or different from one another.

According to such a configuration, it is possible to provide a quinone derivative that can form an electrophotographic photosensitive member having excellent photosensitivity when contained in a photosensitive layer of the electrophotographic photosensitive member.

Preferably, the quinone derivative represented by the general formula (1) is one of quinone derivatives represented by chemical formulae (1-1) to (1-5).

According to such a configuration, solubility in a solvent and compatibility with a binder resin are increased, further improving the photosensitivity.

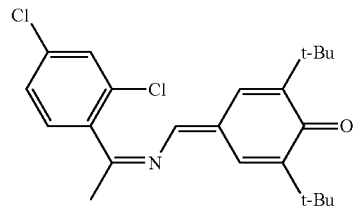

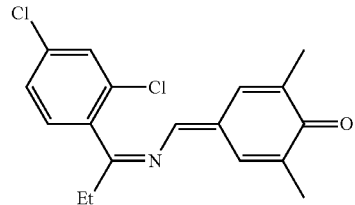

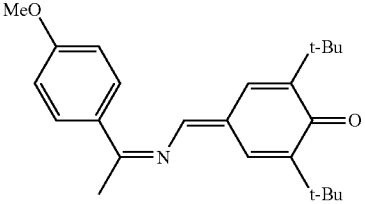

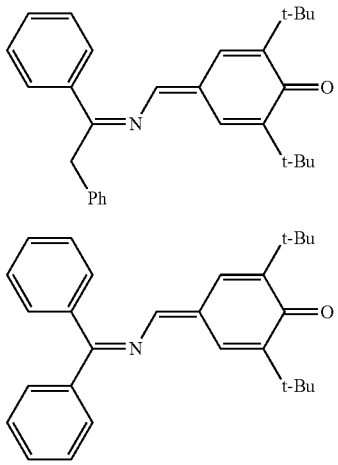

A second embodiment of the present disclosure is an electrophotographic photosensitive member including a conductive substrate and a photosensitive layer, wherein the photosensitive layer contains the quinone derivative according to the first embodiment.

According to such a configuration, it is possible to provide an electrophotographic photosensitive member having excellent photosensitivity.

DETAILED DESCRIPTION

Figure 1A:
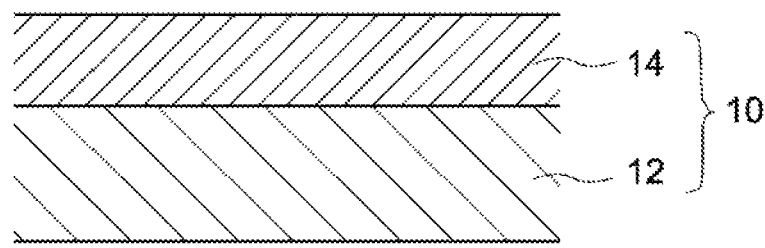
FIGS. 1A to 1C are diagrams for illustrating single-layer electrophotographic photosensitive members according to an embodiment of the present disclosure.

Hereinafter, embodiments of the present disclosure will be described. However, the present disclosure is not limited to the embodiments.

[First Embodiment]

The first embodiment relates to a quinone derivative. The quinone derivative is represented by general formula (1) shown below.

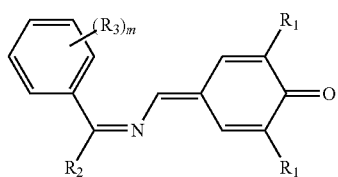

In the general formula (1), $R_1$ and $R_2$ each represent, independently of one another, an alkyl group having a carbon atom number of no less than 1 and no greater than 10, a cycloalkyl group having a carbon atom number of no less than 3 and no greater than 10, an alkoxy group having a carbon atom number of no less than 1 and no greater than 6, an aralkyl group having a carbon atom number of no less than 6 and no greater than 12, or an optionally substituted aryl group having a carbon atom number of no less than 6 and no greater than 14. $R_3$ represents a halogen atom, an optionally substituted alkyl group having a carbon atom number of no less than 1 and no greater than 6, an optionally substituted alkoxy group having a carbon atom number of no less than 1 and no greater than 6, or an optionally substituted aryl group having a carbon atom number of no less than 6 and no greater than 14. m represents an integer of no less than 0 and no greater than 4. When m represents an integer of no less than 2, chemical groups $R_3$ may be the same as or different from one another.

Examples of the alkyl group that is represented by $R_1$ or $R_2$ in the general formula (1) and that has a carbon atom number of no less than 1 and no greater than 10 include a methyl group, an ethyl group, a propyl group, an isopropyl group, an n-butyl group, an isobutyl group, an s-butyl group, a t-butyl group, a pentyl group, an isopentyl group, a neopentyl group, a hexyl group, a heptyl group, an octyl group, a nonyl group, and a decyl group. Of the alkyl groups listed above, a methyl group, an ethyl group (Et-), or a t-butyl group is preferable. The alkyl group preferably has a carbon atom number of no less than 1 and no greater than 6, and more preferably no less than 1 and no greater than 4. The alkyl group is optionally substituted.

Examples of the cycloalkyl group that is represented by $R_1$ or $R_2$ in the general formula (1) and that has a carbon atom number of no less than 3 and no greater than 10 include a cyclopropyl group, a cyclobutyl group, a cyclopentyl group, a cyclohexyl group, a cycloheptyl group, a cyclooctyl group, a cyclononyl group, and a cyclodecyl group. The cycloalkyl group preferably has a carbon atom number of no less than 3 and no greater than 8, and more preferably no less than 3 and no greater than 6. The cycloalkyl group is optionally substituted.

Examples of the alkoxy group that is represented by $R_1$ or $R_2$ in the general formula (1) and that has a carbon atom number of no less than 1 and no greater than 6 include a methoxy group, an ethoxy group, an n-propoxy group, an isopropoxy group, an n-butoxy group, an isobutoxy group, an s-butoxy group, a t-butoxy group, a pentyloxy group, an isopentyloxy group, a neopentyloxy group, and a hexyloxy group. The alkoxy group preferably has a carbon atom number of no less than 1 and no greater than 4, and more preferably no less than 1 and no greater than 3. The alkoxy group may have one or more substituents, and examples of the substituents include an alkyl group.

Examples of the aralkyl group that is represented by $R_1$ or $R_2$ in the general formula (1) and that has a carbon atom number of no less than 6 and no greater than 12 include a benzyl group, an α-methylbenzyl group, a phenethyl group, a styryl group, a cinnamyl group, a 3-phenylpropyl group, a 4-phenylbutyl, a 5-phenylpentyl group, and a 6-phenylhexyl group. Of the aralkyl groups listed above, a benzyl group ($PhCH_2$—) is preferable.

The aryl group that is represented by $R_1$ or $R_2$ in the general formula (1) and that has a carbon atom number of no less than 6 and no greater than 14 include a phenyl group, a tolyl group, a xylyl group, a biphenylyl group, an o-terphenyl group, a naphthyl group, an anthryl group, and a phenanthryl group. Of the aryl groups listed above, a phenyl group is preferable. The aryl group may have one or more substituents, and the number of substituents is preferably one to three. Examples of the substituent include an alkyl group having a carbon atom number of no less than 1 and no greater than 10.

Examples of the halogen atom represented by $R_3$ in the general formula (1) include a fluorine atom, a chlorine atom, a bromine atom, and an iodine atom. Of the halogen atoms listed above, a chlorine atom is preferable.

Examples of the alkyl group that is represented by $R_3$ in the general formula (1) and that has a carbon atom number of no less than 1 and no greater than 6 include a methyl group, an ethyl group, a propyl group, an isopropyl group, an n-butyl group, an isobutyl group, an s-butyl group, a t-butyl group, a pentyl group, an isopentyl group, a neopentyl group, and a hexyl group. The alkyl group preferably has a carbon atom number of no less than 1 and no greater than 4, and more preferably no less than 1 and no greater than 3. The alkyl group is optionally substituted.

Examples of the alkoxy group that is represented by $R_3$ in the general formula (1) and that has a carbon atom number of no less than 1 and no greater than 6 include a methoxy group, an ethoxy group, an n-propoxy group, an isopropoxy group, an n-butoxy group, an isobutoxy group, an s-butoxy group, a t-butoxy group, a pentyloxy group, an isopentyloxy group, a neopentyloxy group, and a hexyloxy group. Of the alkoxy group listed above, a methoxy group is preferable. The alkoxy group preferably has a carbon atom number of no less than 1 and no greater than 4, and more preferably no less than 1 and no greater than 3. The alkoxy group may have one or more substituents, and examples of the substituents include an alkyl group.

Examples of the aryl group that is represented by $R_3$ in the general formula (1) and that has a carbon atom number of no less than 6 and no greater than 14 include a phenyl group, a tolyl group, a xylyl group, a biphenylyl group, an o-terphenyl group, a naphthyl group, an anthryl group, and a phenanthryl group. The aryl group may have one or more substituents, and the number of substituents is preferably one to three. Examples of the substituent include an alkyl group, an aralkyl group, an alkoxy group, an alkanoyl group, a halogen atom, and an alkoxycarbonyl group.

m represents an integer of no less than 0 and no greater than 4. Preferably, m represents an integer of no less than 0 and no greater than 3. More preferably, m represents an integer of no less than 0 and no greater than 2. When m represents an integer of no less than 2, chemical groups $R_3$ may be the same as or different from one another.

Preferable examples of the quinone derivative represented by the general formula (1) include quinone derivatives represented by chemical formulae (1-1) to (1-5) (hereinafter, may be referred to as quinone derivatives (1-1) to (1-5)).

1-1

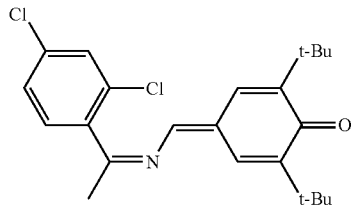

-continued 1-2

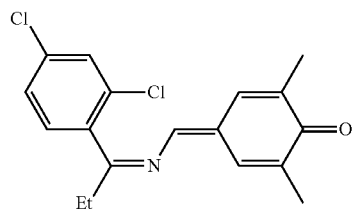

1-3

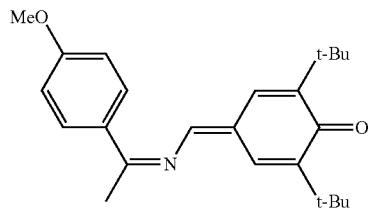

1-4

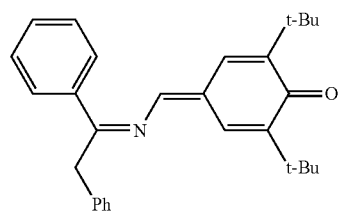

1-5

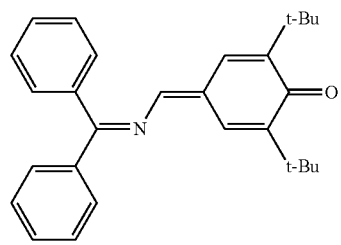

Next, a method for preparing the quinone derivative represented by the general formula (1) (hereinafter, may be referred to as a quinone derivative (1)) will be described.

A method for preparing the quinone derivative (1-1) from among the quinone derivatives (1-1) to (1-5) will be described as a representative example of the method for preparing the quinone derivative (1). Methods for preparing the quinone derivatives (1-2) to (1-5) will be described in Synthesis Examples 2 to 5 in Examples.

[Synthesis of Quinone Derivative (1-1)]

The quinone derivative (1-1) can be prepared through reaction (a) and reaction (b) represented by scheme (1).

Scheme (1)

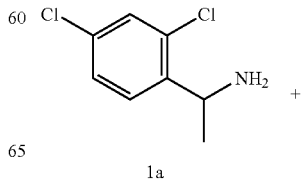

1a

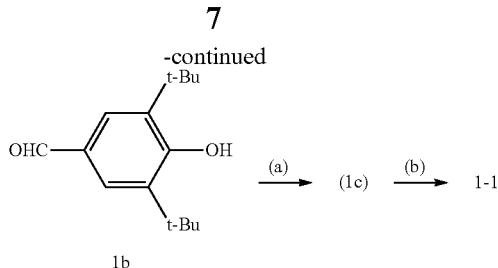

[Reaction (a): Synthesis of Compound (1c)]

A specified amount of p-toluenesulfonic acid is added to a solution obtained by dissolving a compound (1a) and a compound (1b) in an organic solvent such as toluene, and the resulting solution is refluxed with removal of water for a specified period of time. Next, extraction into an organic layer is performed with addition of water, and the organic layer is dried. Subsequently, the solvent is evaporated under reduced pressure to give a compound (1c) in the form of an oil. The compound (1c) in the form of an oil is used in the reaction (b) without being refined.

A reaction ratio (molar ratio) of the compound (1a) and the compound (1b) is preferably 3:1 to 1:3, and more preferably 2:1 to 1:2.

[Reaction (b): Synthesis of Quinone Derivative (1-1)]

A specific amount of silver oxide is added to a solution obtained by dissolving the compound (1c) in the form of an oil in an organic solvent such as chloroform, and the resulting solution is stirred at room temperature (for example, 25° C.) for a specified period of time to cause oxidation reaction. After the oxidation reaction, the silver oxide is separated from the solution through filtration, and the resulting filtrate is purified by column chromatography or the like to give the quinone derivative (1-1).

The other quinone derivatives (1) of the present disclosure can be prepared in accordance with the scheme (1).

As mentioned above, the quinone derivative (1) thus obtained can be favorably used as an electron transport material in a photosensitive layer of an electrophotographic photosensitive member. Furthermore, the quinone derivative (1) can be used in various fields such as the field of solar cells and the field of electroluminescence elements.

[Second Embodiment]

The second embodiment relates to an electrophotographic photosensitive member (hereinafter, may be referred to as a photosensitive member). The photosensitive member according to the second embodiment includes a conductive substrate and a photosensitive layer. The photosensitive layer contains the quinone derivative (1).

Hereinafter, the second embodiment will be described in detail mainly with respect to differences from what has been described in the first embodiment.

Electrophotographic photosensitive members are broadly divided into single-layer electrophotographic photosensitive members (hereinafter, may be referred to as single-layer photosensitive members) and multi-layer electrophotographic photosensitive members (hereinafter, may be referred to as multi-layer photosensitive members). Preferably, the present disclosure is applied to a single-layer photosensitive member, because single-layer photosensitive members are for example simple in structure, easily producible, effectively prevented from having film defects during formation of their photosensitive layers, fewer in interfaces between layers, and easily improved in optical properties.

Hereinafter, single-layer photosensitive members will be described.

<<Single-Layer Electrophotographic Photosensitive Member>>

(Basic Configuration)

Figure 1B:
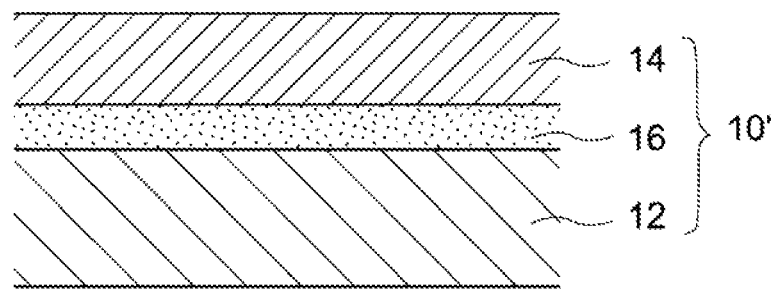
Figure 1C:
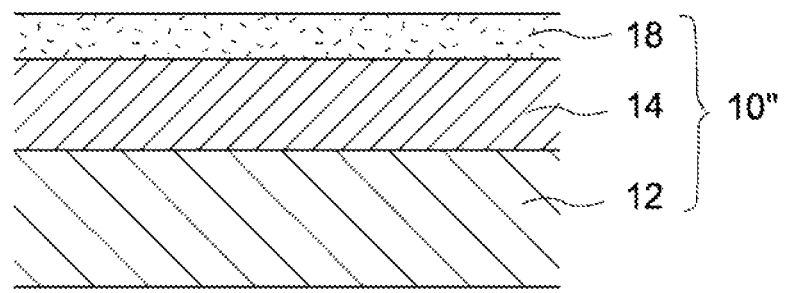

Structure of single-layer photosensitive members will be described with reference to FIGS. 1A to 1C. As illustrated in FIG. 1A, a single-layer photosensitive member 10 for example includes a conductive substrate 12 and a photosensitive layer 14. The photosensitive layer 14 is formed directly on the conductive substrate 12. FIG. 1B illustrates a single-layer photosensitive member 10' further including an intermediate layer (more specifically, an undercoat layer or a barrier layer). As illustrated in FIG. 1B, an intermediate layer 16 may be formed in the photosensitive member 10' to the extent that the intermediate layer 16 does not interfere with the properties of the photosensitive member.

The photosensitive layer 14 may be formed indirectly on the conductive substrate 12 with the intermediate layer 16 therebetween. FIG. 1C illustrates a single-layer photosensitive member 10" including another layer as an outermost layer (for example, a protective layer). As illustrated in FIG. 1C, the single-layer photosensitive member 10" may include a protective layer 18 as the outermost layer.

The single-layer photosensitive member may have a configuration of the photosensitive member 10' in which the barrier layer 16 is formed between the conductive substrate 12 and the photosensitive layer 14 as illustrated in FIG. 1B to the extent that the barrier layer 16 does not interfere with the properties of the photosensitive member. Alternatively, the single-layer photosensitive member may have a configuration of the photosensitive member 10" in which the protective layer 18 is formed on the surface of the photosensitive layer 14 as illustrated in FIG. 1C.

These single-layer photosensitive members are simple in layer structure and highly producible.

These single-layer photosensitive members are also excellent in photosensitivity as a result of containing the quinone derivative (1).

Furthermore, hole transfer between a charge generating material and a hole transport material contained in the photosensitive layers of these single-layer photosensitive members is effective, improving stability of sensitivity. Hereinafter, the conductive substrate and the photosensitive layer will be described.

(Conductive Substrate)

No particular limitations are placed on the conductive substrate other than being a conductive substrate that can be used in a photosensitive member. The conductive substrate may be formed from a material that is conductive at least at a surface thereof. The conductive substrate may be for example a conductive substrate formed from a conductive material or a conductive substrate having a coat of a conductive material. Examples of conductive materials that may be used include metals such as iron, aluminum, copper, tin, platinum, silver, vanadium, molybdenum, chromium, cadmium, titanium, nickel, palladium, indium, stainless steel, and brass; and alloys. Examples of conductive substrates having a coat of a conductive material include conductive substrates made from a plastic material having a metal vapor-deposited or laminated thereon and conductive substrates made from glass covered by aluminum iodide, tin oxide, indium oxide, or the like.

Shape of the conductive substrate is not particularly limited and can be selected as appropriate in accordance with the structure of an image forming apparatus in which the conductive substrate is to be used. Examples of the shape of the conductive substrate include a sheet or a drum. The conductive substrate preferably has sufficient mechanical strength during use.
(Photosensitive Layer)

The photosensitive layer contains a charge generating material, a hole transport material, an electron transport material, and a binder resin in a single layer. The electron transport material includes the quinone derivative (1). The photosensitive layer in the single-layer photosensitive member preferably has a thickness of no less than 5 µm and no greater than 100 µm, and more preferably no less than 10 µm and no greater than 50 µm. Hereinafter, the charge generating material, the hole transport material, the electron transport material, and the binder resin will be described.
(Charge Generating Material)

No particular limitations are placed on the charge generating material other than being a charge generating material that can be used in photosensitive members. Examples of charge generating materials that may be used include organic charge generating materials and inorganic charge generating materials. Examples of organic charge generating materials that may be used include phthalocyanine-based pigments, perylene-based pigments, bisazo pigments, diketopyrrolopyrrole pigments, metal-free naphthalocyanine pigments, metal naphthalocyanine pigments, squaraine pigments, tris-azo pigments, indigo pigments, azulenium pigments, cyanine pigments, pyrylium pigments, anthanthrone pigments, triphenylmethane-based pigments, threne pigments, toluidine-based pigments, pyrazoline-based pigments, and quinacridone-based pigments. Examples of inorganic charge generating materials that may be used include selenium, selenium-tellurium, selenium-arsenic, cadmium sulfide, and amorphous silicon. Examples of phthalocyanine-based pigments that may be used include metal-free phthalocyanine (for example, τ-form or X-form), titanyl phthalocyanine (for example, α-form or Y-form), hydroxygallium phthalocyanine (for example, V-form), and chlorogallium phthalocyanine (for example, II-form). Of the charge generating materials listed above, X-form metal-free phthalocyanine or Y-form titanyl phthalocyanine is preferable. The charge generating materials listed above may be used independently, or two or more of the charge generating materials may be used in combination. Photosensitive members including both a hole transport material and an electron transport material can be improved in photosensitivity and stability by selecting appropriate charge generating materials.

Furthermore, any one of the charge generating materials listed above or a combination of two or more of the charge generating materials that is absorptive with respect to light in a desired wavelength region may be selected as appropriate. For example, in a digital optical image forming apparatus (for example, a laser beam printer or facsimile machine that uses a light source such as a semiconductor laser), a photosensitive member that is sensitive to a region of wavelengths of at least 700 nm is needed. Therefore, the photosensitive member preferably includes for example at least one of metal-free phthalocyanine, titanyl phthalocyanine, hydroxygallium phthalocyanine, and chlorogallium phthalocyanine.

In an analogue optical image forming apparatus (for example, an electrostatic process copier including a white light source such as a halogen lamp), a photosensitive member that is sensitive to a visible region is needed. For example, therefore, a perylene-based pigment or a bisazo pigment is favorably used.

(Hole Transport Material)

Examples of hole transport materials that may be used include oxadiazole-based compounds such as 2,5-di(4-methylaminophenyl)-1,3,4-oxadiazole; styryl-based compounds such as 9-(4-diethylaminostyryl)anthracene; carbazole-based compounds such as polyvinyl carbazole; organic polysilane compounds; pyrazoline-based compounds such as 1-phenyl-3-(p-dimethylaminophenyl)pyrazoline; hydrazone-based compounds; triphenyl amine-based compounds; nitrogen containing cyclic compounds such as oxazole-based compounds, isoxazole-based compounds, thiazole-based compounds, imidazole-based compounds, pyrazole-based compounds, and triazole-based compounds; and nitrogen containing condensed polycyclic compounds such as indole-based compounds and thiadiazole-based compounds. The hole transport materials listed above may be used independently, or two or more of the hole transport materials may be used in combination.

The charge generating material is preferably contained in an amount of no less than 0.1 parts by mass and no greater than 50 parts by mass relative to 100 parts by mass of the binder resin, and more preferably in an amount of no less than 0.5 parts by mass and no greater than 30 parts by mass.
(Electron Transport Material)

The quinone derivative (1) is as described above. The quinone derivative (1) is preferably contained in an amount of no less than 5 parts by mass and no greater than 100 parts by mass relative to 100 parts by mass of the binder resin, and more preferably no less than 10 parts by mass and no greater than 80 parts by mass.

The electrophotographic photosensitive member of the present disclosure contains the quinone derivative (1) as an electron transport material. The photosensitive layer of the electrophotographic photosensitive member may further contain a known electron transport material in addition to the quinone derivative (1).

Examples of electron transport materials that may be contained in addition to the quinone derivative (1) include quinone derivatives (quinone derivatives other than the quinone derivative (1)), anthraquinone derivatives, malononitrile derivatives, thiopyran derivatives, trinitrothioxanthone derivatives, 3,4,5,7-tetranitro-9-fluorenone derivatives, dinitroanthracene derivatives, dinitroacridine derivatives, nitroanthraquinone derivatives, dinitroanthraquinone derivatives, tetracyanoethylene, 2,4,8-trinitrothioxanthone, dinitrobenzene, dinitroanthracene, dinitroacridine, nitroanthraquinone, dinitroanthraquinone, succinic anhydride, maleic anhydride, and dibromomaleic anhydride. The electron transport materials listed above may be used independently, or two or more of the electron transport materials may be used in combination.
(Binder Resin)

The binder resin allows the charge generating material and other components to be dispersed and fixed in the photosensitive layer. Examples of binder resins that may be used include thermoplastic resins, thermosetting resins, and photocurable resins. Examples of thermoplastic resins that may be used include polycarbonate resins (for example, bisphenol Z polycarbonate resin, bisphenol ZC polycarbonate resin, bisphenol C polycarbonate resin, and bisphenol A polycarbonate resin), polyarylate resins, styrene-butadiene copolymers, styrene-acrylonitrile copolymers, styrene-maleic acid copolymers, acrylic acid-based copolymers, styrene-acrylic acid-based copolymers, polyethylene resins, ethylene-vinyl acetate copolymers, chlorinated polyethylene resins, polyvinyl chloride resins, polypropylene resins, ionomer resins, vinyl chloride-vinyl acetate copolymers, alkyd resins, polyamide resins, polyurethane resins, polysulfone resins, diallyl phthalate resins, ketone resins, polyvinyl butyral resins, and polyether resins. Examples of thermosetting resins that may be used include silicone resins, epoxy resins, phenolic resins, urea resins, melamine resins, and other crosslinkable thermosetting resins. Examples of photocurable resins that may be used include epoxy-acrylic acid-based copolymers and urethane-acrylic acid-based copolymers. The binder resins listed above may be used independently, or two or more of the binder resins may be used in combination.

(Additive)

Various known additives such as antidegradants (for example, antioxidants, radical scavengers, quenchers, and ultraviolet absorbing agents), softeners, plasticizers, surface modifiers, extending agents, thickeners, dispersion stabilizers, waxes, acceptors, and donors may be contained in the photosensitive layer in addition to the other components so long as such additives do not adversely affect electrophotographic properties of the photosensitive member. A sensitizer may be used in combination with the charge generating material in order to improve sensitivity of the photosensitive layer. Examples of sensitizers that may be used include known sensitizers such as terphenyl, halonaphthoquinones, and acenaphthylene. A surfactant or a leveling agent may be used in order to improve dispersibility of the electron transport material and the charge generating material and surface smoothness of the photosensitive layer.

(Method for Manufacturing Single-Layer Photosensitive Member)

A method for manufacturing a photosensitive member will be described using a single-layer photosensitive member as a representative example. The single-layer photosensitive member is for example manufactured as described below. The single-layer photosensitive member is manufactured by forming a photosensitive layer on a conductive substrate. The photosensitive layer is formed by applying an application liquid for photosensitive layer formation (hereinafter, may be referred to as an application liquid) onto a conductive substrate and drying the application liquid thereon. More specifically, the photosensitive member is formed as follows. First, the application liquid is prepared. The application liquid is prepared by dissolving or dispersing in a solvent a charge generating material, a hole transport material, the quinone derivative (1) as an electron transport material, a binder resin, and additives as necessary. The application liquid thus prepared is applied onto the conductive substrate and dried thereon to form a photosensitive layer, thereby manufacturing a single-layer photosensitive member.

The application liquid is prepared by mixing and dispersing the components in the solvent. For mixing and dispersing the components, for example, a bead mill, a roll mill, a ball mill, an attritor, a paint shaker, or an ultrasonic disperser can be used.

The application liquid may contain for example a surfactant in order to improve dispersibility of the components.

No particular limitations are placed on the method by which the application liquid is applied so long as the method enables uniform application of an application liquid onto a conductive substrate. Examples of application methods that may be used include dip coating, spray coating, spin coating, and bar coating.

No particular limitations are placed on the method by which the application liquid is dried other than being a method for evaporating a solvent contained in an application liquid. The method of drying may for example be heat treatment (hot-air drying) using a high-temperature dryer or a reduced pressure dryer. The heat treatment is for example performed for no less than 3 minutes and no greater than 120 minutes at a temperature of no less than 40° C. and no greater than 150° C.

Various organic solvents may be used as the solvent. Examples thereof include alcohols (for example, methanol, ethanol, isopropanol, and butanol), aliphatic hydrocarbons (for example, n-hexane, octane, and cyclohexane), and aromatic hydrocarbons (for example, benzene, toluene, and xylene), halogenated hydrocarbons (for example, dichloromethane, dichloroethane, chloroform, carbon tetrachloride, and chlorobenzene), ethers (for example, dimethyl ether, diethyl ether, tetrahydrofuran, ethylene glycol dimethyl ether, and diethylene glycol dimethyl ether), ketones (for example, acetone, methyl ethyl ketone, and cyclohexanone), esters (for example, ethyl acetate and methyl acetate), and some other solvents (for example, dimethyl formaldehyde, dimethyl formamide, and dimethyl sulfoxide). The solvents listed above may be used independently, or two or more of the solvents may be used in combination.

The photosensitive member of the present disclosure can be used as an image bearing member of an electrophotographic image forming apparatus. No particular limitation is placed on the image forming apparatus other than being an image forming apparatus that uses electrophotography. Examples of such image forming apparatuses include electrostatic process copiers, facsimile machines, and laser beam printers.

EXAMPLES

The following provides more specific explanation of the present disclosure through use of Examples. However, it should be noted that the present disclosure is not limited to the scope of the Examples.

Prior to manufacture of photosensitive members of Examples and Comparative Examples, the following materials were synthesized.

[Synthesis of Electron Transport Material]

The quinone derivatives (1-1) to (1-5) were synthesized as electron transport material to be used in Examples.

Synthesis Example 1

Synthesis of Quinone Derivative (1-1)

The quinone derivative (1-1) was prepared through reaction (a) and reaction (b) represented by scheme (1).

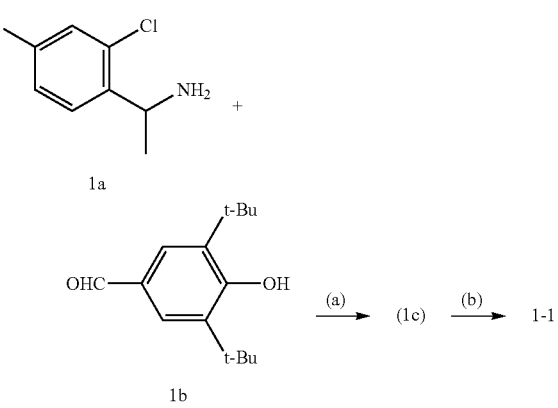

[Reaction (a): Synthesis of Compound (1c)]

First, 0.1 mole equivalents of p-toluenesulfonic acid was added to a solution obtained by dissolving 1.90 g (0.01 mol) of a compound (1a) and 2.34 g (0.01 mol) of a compound (1b) in 50 mL of toluene, and the resulting solution was refluxed for 5 hours with removal of water using a reaction tube equipped with a Dean-Stark trap. After a reaction in the reaction tube was complete, extraction into an organic layer was performed with addition of water, and the organic layer was dried. Subsequently, the toluene was evaporated under reduced pressure to give a compound (1c) in the form of an oil. The compound (1c) in the form of an oil was used in the reaction (b) without being refined.

[Reaction (b): Synthesis of Quinone Derivative (1-1)]

Figure 2:
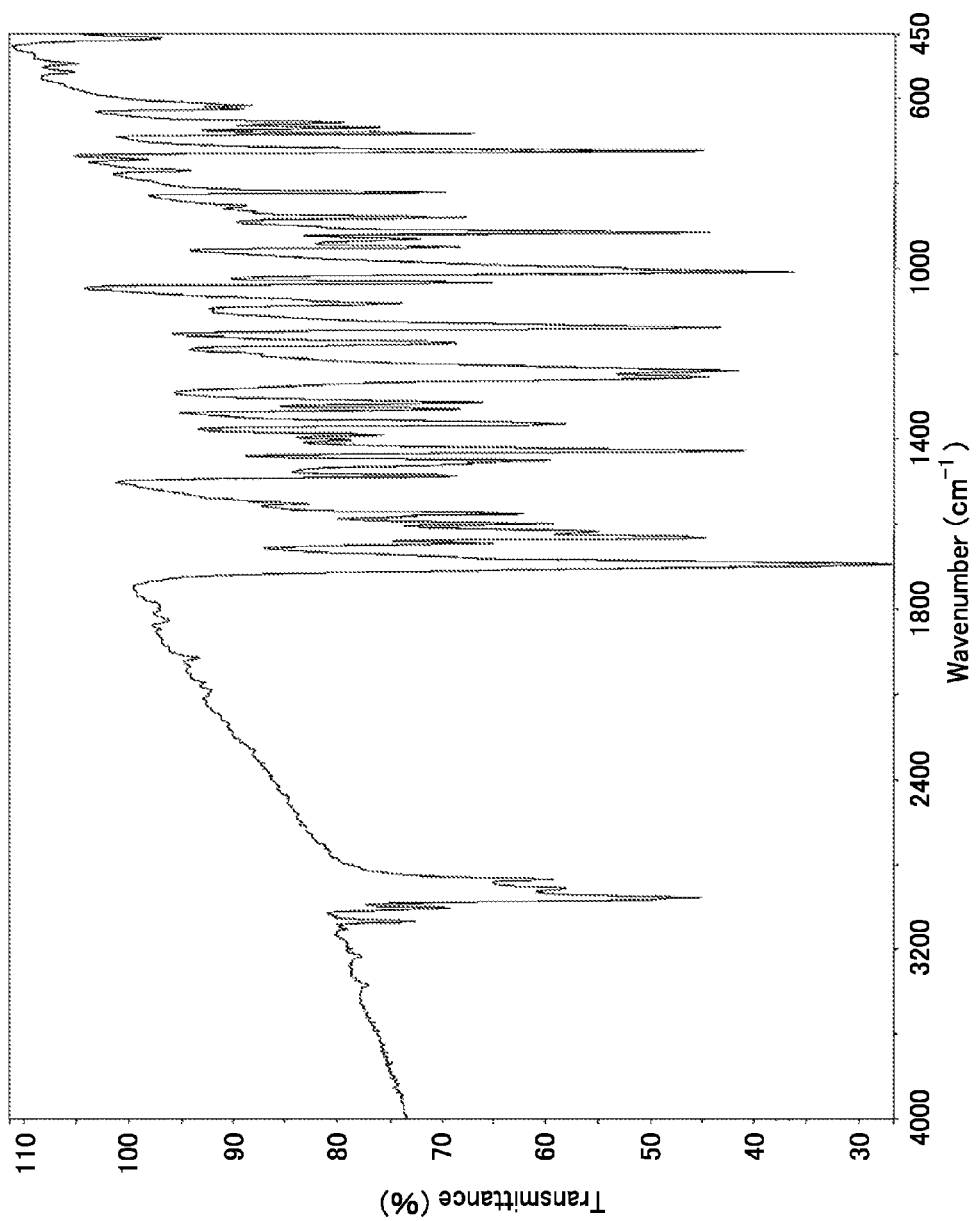
FIG. 2 is a graph showing an infrared absorption spectrum (IR spectrum) of a quinone derivative (1-1) according to an embodiment of the present disclosure.

First, 2.46 g (0.02 mol) of silver oxide was added to a solution obtained by dissolving the compound (1c) in the form of an oil in 100 mL of chloroform, and the resulting solution was stirred at room temperature for 5 hours to cause oxidation reaction. After the oxidation reaction, the silver oxide was separated from the chloroform solution through filtration, and the resulting filtrate was purified by silica gel column chromatography (developing solvent: chloroform/hexane) to give 2.42 g of the quinone derivative (1-1) (percentage yield: approximately 60%). FIG. 2 shows an infrared absorption spectrum (IR spectrum) of the quinone derivative (1-1) that was obtained through infrared spectroscopy (KBr pellet method). It was confirmed that the compound synthesized as described above was the quinone derivative (1-1) based on the IR spectrum.

Synthesis Example 2

Synthesis of Quinone Derivative (1-2)

The quinone derivative (1-2) was prepared through reaction (a) and reaction (b) represented by scheme (2). Specifically, 1.67 g (percentage yield: approximately 50%) of the quinone derivative (1-2) was obtained in the same manner as in accordance with the scheme (1) except that 1.90 g (0.01 mol) of the compound (1a) was changed to 2.04 g (0.01 mol) of a compound (2a) and 2.34 g (0.01 mol) of the compound (1b) was changed to 1.5 g (0.01 mol) of a compound (2b). It was confirmed that the compound synthesized as described above was the quinone derivative (1-2) based on an IR spectrum as for the quinone derivative (1-1).

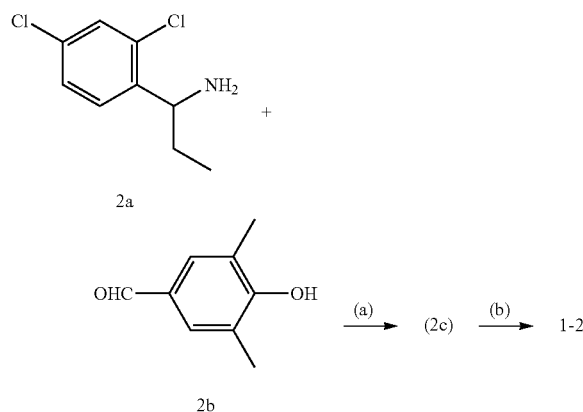

Scheme (2)

Synthesis Example 3

Synthesis of Quinone Derivative (1-3)

The quinone derivative (1-3) was prepared through reaction (a) and reaction (b) represented by scheme (3). Specifically, 2.01 g (percentage yield: approximately 55%) of the quinone derivative (1-3) was obtained in the same manner as in accordance with the scheme (1) except that 1.90 g (0.01 mol) of the compound (1a) was changed to 1.51 g (0.01 mol) of a compound (3a) and 2.34 g (0.01 mol) of the compound (1b) was changed to 2.34 g (0.01 mol) of a compound (3b). It was confirmed that the compound synthesized as described above was the quinone derivative (1-3) based on an IR spectrum as for the quinone derivative (1-1).

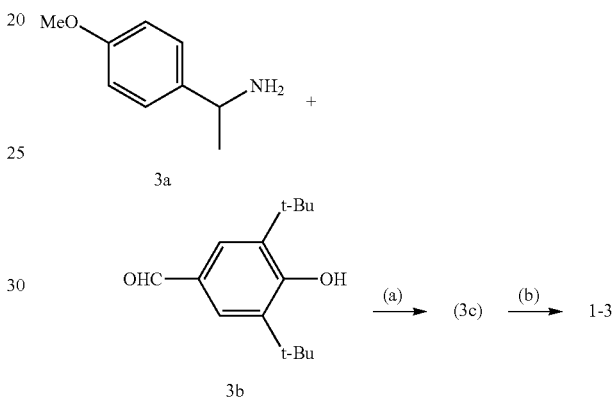

Scheme (3)

Synthesis Example 4

Synthesis of Quinone Derivative (1-4)

The quinone derivative (1-4) was prepared through reaction (a) and reaction (b) represented by scheme (4). Specifically, 2.47 g (percentage yield: approximately 60%) of the quinone derivative (1-4) was obtained in the same manner as in accordance with the scheme (1) except that 1.90 g (0.01 mol) of the compound (1a) was changed to 1.97 g (0.01 mol) of a compound (4a) and 2.34 g (0.01 mol) of the compound (1b) was changed to 2.34 g (0.01 mol) of a compound (4b). It was confirmed that the compound synthesized as described above was the quinone derivative (1-4) based on an IR spectrum as for the quinone derivative (1-1).

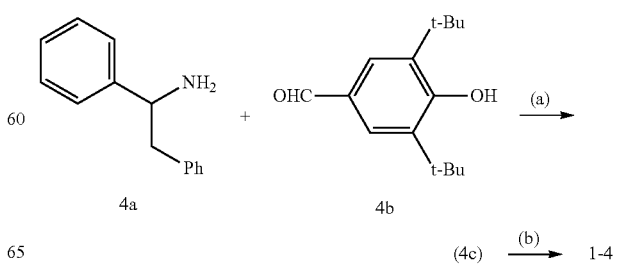

Scheme (4)

Synthesis Example 5

Synthesis of Quinone Derivative (1-5)

Figure 3:
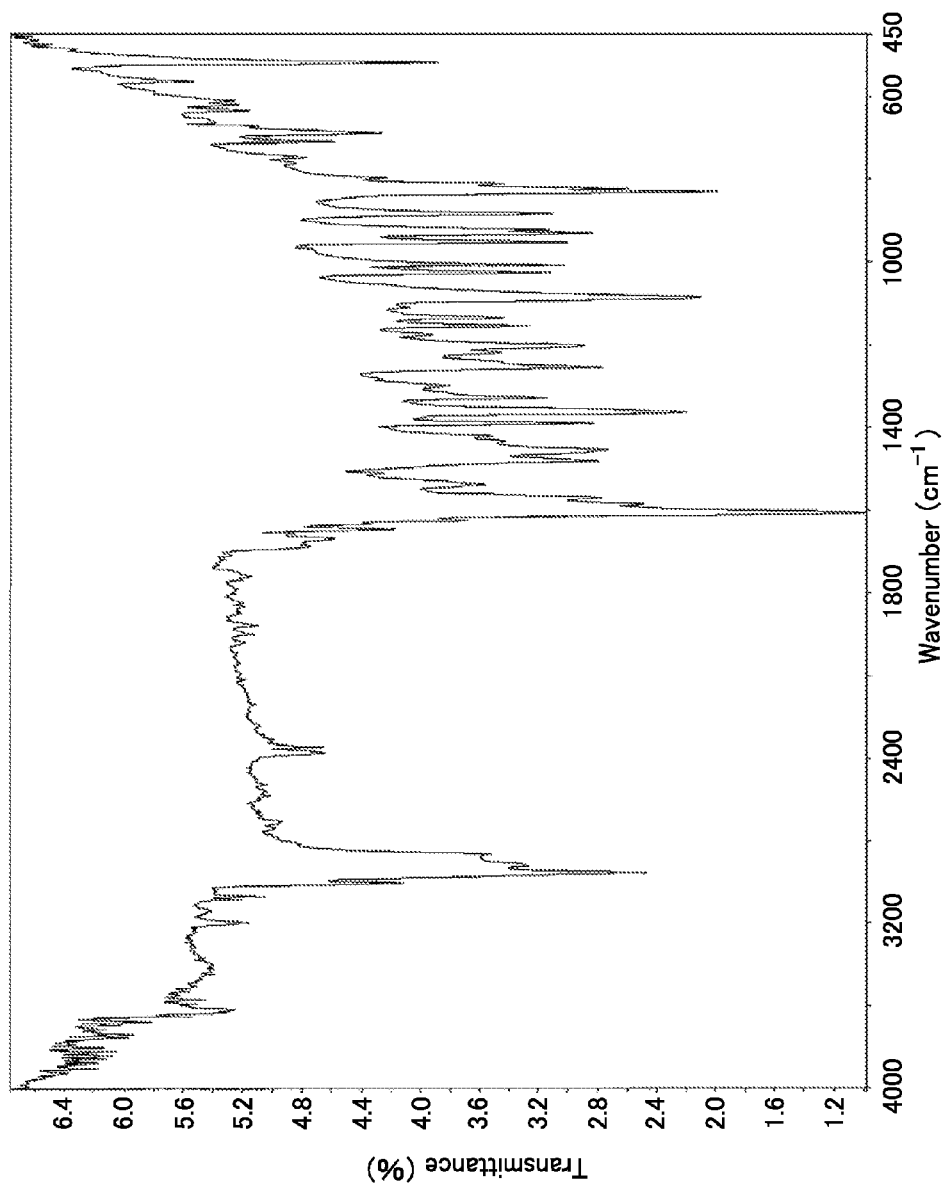
FIG. 3 is a graph showing an IR spectrum of a quinone derivative (1-5) according to an embodiment of the present disclosure.

The quinone derivative (1-5) was prepared through reaction (a) and reaction (b) represented by scheme (5). Specifically, 1.99 g (percentage yield: approximately 50%) of the quinone derivative (1-5) was obtained in the same manner as in accordance with the scheme (1) except that 1.90 g (0.01 mol) of the compound (1a) was changed to 1.83 g (0.01 mol) of a compound (5a) and 2.34 g (0.01 mol) of the compound (1b) was changed to 2.34 g (0.01 mol) of a compound (5b). FIG. 3 shows an infrared absorption spectrum (IR spectrum) of the quinone derivative (1-5) that was obtained through infrared spectroscopy (KBr pellet method). It was confirmed that the compound synthesized as described above was the quinone derivative (1-5) based on the IR spectrum.

Scheme (5)

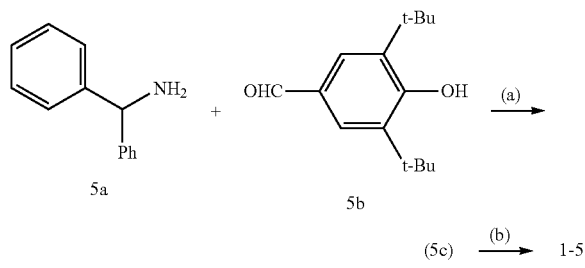

<<Preparation of Single-Layer Electrophotographic Photosensitive Member>>

Next, single-layer electrophotographic photosensitive members of Examples and Comparative Examples were prepared and evaluated.

First, the following materials were prepared.

[Charge Generating Material]

An X-form metal-free phthalocyanine and a Y-form titanyl phthalocyanine were prepared as charge generating materials.

[Hole Transport Material]

A compound represented by chemical formula (H-1) was prepared as a hole transport material (hereinafter, may be referred to as a hole transport material (H-1)).

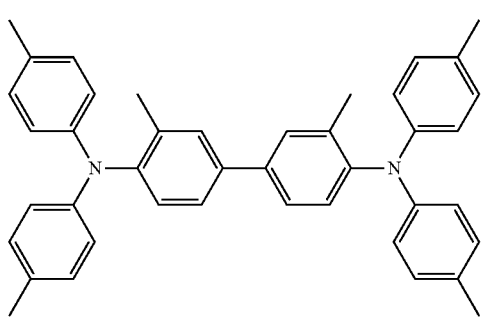

[Electron Transport Material]

A phenylbenzofuranone derivative represented by chemical formula (E-1) (hereinafter, may be referred to as a phenylbenzofuranone derivative (E-1)) was prepared as an electron transport material to be used in Comparative Examples.

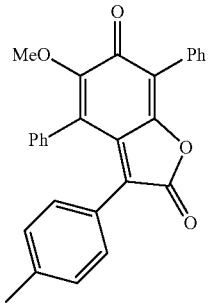

As shown in Table 1 below, the X-form metal-free phthalocyanine or the Y-form titanyl phthalocyanine as a charge generating material, the hole transport material (H-1), and one of the quinone derivatives (1-1) to (1-5) and the phenylbenzofuranone derivative (E-1) as an electron transport material were used to prepare each of the single-layer electrophotographic photosensitive members of Examples 1 to 10, and Comparative Examples 1 and 2.

Example 1

First, 5 parts by mass of the X-form metal-free phthalocyanine as a charge generating material, 50 parts by mass of the hole transport material (H-1), 30 parts by mass of the quinone derivative (1-1) as an electron transport material, and 100 parts by mass of a bisphenol Z polycarbonate resin (viscosity average molecular weight: 50,000) as a binder resin were added to 800 parts by mass of a solvent (tetrahydrofuran). Next, the materials were mixed and dispersed in the solvent for 50 hours using a ball mill to give an application liquid for photosensitive layer formation. The application liquid for photosensitive layer formation was applied onto a conductive substrate made from an anodized aluminum tube (diameter: 30 mm, total length: 238.5 mm) by dip coating and subjected to hot-air drying at 100° C. for 40 minutes. Thus, a single-layer photosensitive member (diameter: 30 mm) including the conductive substrate and a photosensitive layer having a thickness of 30 μm formed on the conductive substrate was prepared.

Examples 2 to 10, and Comparative Examples 1 and 2

A single-layer photosensitive member was manufactured in the same manner as in Example 1 except that the combination of the charge generating material and the electron transport material was changed as shown in Table 1. In the "electron transport material" column in Table 1, 1-1 to 1-5 represent the quinone derivatives (1-1) to (1-5), respectively, and E-1 represents the phenylbenzofuranone derivative (E-1). In the "hole transport material" column in Table 1, H-1 represents the hole transport material (H-1).

TABLE 1

| | Charge generating material | Hole transport material | Electron transport material | Vr (V) |
|---|---|---|---|---|
| Example 1 | X-form metal-free phthalocyanine | H-1 | 1-1 | +140 |
| Example 2 | Y-form titanyl phthalocyanine | | | +147 |
| Example 3 | X-form metal-free phthalocyanine | | 1-2 | +143 |
| Example 4 | Y-form titanyl phthalocyanine | | | +150 |
| Example 5 | X-form metal-free phthalocyanine | | 1-3 | +149 |
| Example 6 | Y-form titanyl phthalocyanine | | | +155 |
| Example 7 | X-form metal-free phthalocyanine | | 1-4 | +142 |
| Example 8 | Y-form titanyl phthalocyanine | | | +149 |
| Example 9 | X-form metal-free phthalocyanine | | 1-5 | +145 |
| Example 10 | Y-form titanyl phthalocyanine | | | +152 |
| Comparative Example 1 | X-form metal-free phthalocyanine | H-1 | E-1 | +186 |
| Comparative Example 2 | Y-form titanyl phthalocyanine | | | +197 |

<<Evaluation>>

Photosensitivity of the single-layer photosensitive members of Examples 1 to 10, and Comparative Examples 1 and 2 was evaluated according to the following criteria. The evaluation results are shown in Table 1.

(Photosensitivity Evaluation)

Photosensitivity of each photosensitive member was measured using a drum sensitivity test device produced by Gen-Tech, Inc. Specifically, the peripheral surface of each photosensitive member was charged to a peripheral surface potential of +700 V through application of a voltage. Next, light exposure was performed on the charged photosensitive member through irradiation with light for 80 milliseconds. The light used for the light exposure was monochromatic light having a wavelength of 780 nm, a half-width of 20 nm, and a light intensity of 0.4 μJ/cm² extracted from white light emitted by a halogen lamp using a band pass filter. Surface potential of the photosensitive member was measured after a lapse of 330 milliseconds from the start of the light exposure and taken to be a residual potential Vr (unit: V). A smaller residual potential Vr indicates better photosensitivity.

As shown in Table 1, the photosensitive layer in each of the single-layer photosensitive members of Examples 1 to 10 contained one of the quinone derivatives (1-1) to (1-5) as an electron transport material. The photosensitive layer of each of the single-layer photosensitive members of Comparative Examples 1 and 2 contained the phenylbenzofuranone derivative (E-1) as an electron transport material. Table 1 shows that the single-layer photosensitive members of Examples 1 to 10 each resulted in a residual potential Vr of no less than +140 V and no greater than +155 V. The single-layer photosensitive members of Comparative Examples 1 and 2 each resulted in a residual potential Vr of no less than +186 V and no greater than +197 V. The results have revealed that the single-layer photosensitive members of Examples 1 to 10 each containing the quinone derivative (1) had better photosensitivity than the single-layer photosensitive members of Examples 1 and 2 each containing the phenylbenzofuranone derivative (E-1).

What is claimed is:

1. A quinone derivative represented by general formula (1) shown below,

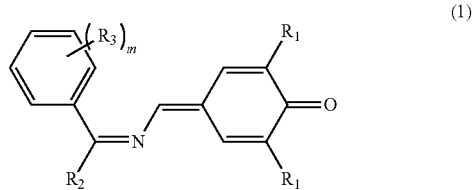

where, in the general formula (1), $R_1$ represents an alkyl group having a carbon atom number of no less than 1 and no greater than 10, a cycloalkyl group having a carbon atom number of no less than 3 and no greater than 10, an alkoxy group having a carbon atom number of no less than 1 and no greater than 6, an aralkyl group having a carbon atom number of no less than 6 and no greater than 12, or an optionally substituted aryl group having a carbon atom number of no less than 6 and no greater than 14, $R_2$ represents an alkyl group having a carbon atom number of no less than 1 and no greater than 10, a cycloalkyl group having a carbon atom number of no less than 3 and no greater than 10, an alkoxy group having a carbon atom number of no less than 1 and no greater than 6, or an aralkyl group having a carbon atom number of no less than 6 and no greater than 12, $R_3$ represents a halogen atom, an optionally substituted alkyl group having a carbon atom number of no less than 1 and no greater than 6, an optionally substituted alkoxy group having a carbon atom number of no less than 1 and no greater than 6, or an optionally substituted aryl group having a carbon atom number of no less than 6 and no greater than 14, m represents an integer of no less than 0 and no greater than 4, and when m represents an integer of no less than 2, chemical groups $R_3$ may be the same as or different from one another.

2. The quinone derivative according to claim 1, wherein the quinone derivative is any one of quinone derivatives represented by chemical formula (1-1) to (1-4) shown below

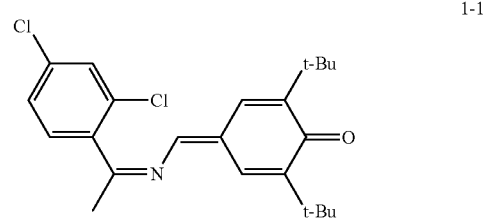

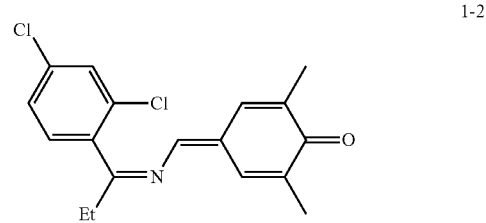

-continued

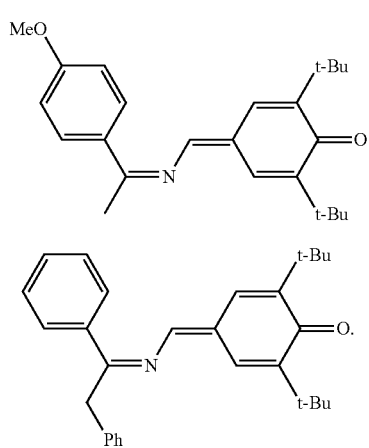

1-3

1-4

3. The quinone derivative according to claim 2, wherein the quinone derivative is represented by the chemical formula (1-1), (1-2), or (1-4).

4. An electrophotographic photosensitive member comprising a conductive substrate and a photosensitive layer, wherein
the photosensitive layer contains the quinone derivative according to claim 1.

5. The electrophotographic photosensitive member according to claim 4, wherein
the photosensitive layer is a single-layer type photosensitive layer in which a charge generating material, a hole transport material, an electron transport material, and a binder resin are contained in the same layer as one another, and
the electron transport material includes the quinone derivative.

* * * * *